United States Patent
Van Berkel et al.

(10) Patent No.: US 9,779,926 B2
(45) Date of Patent: Oct. 3, 2017

(54) METHOD AND SYSTEM FOR FORMATION AND WITHDRAWAL OF A SAMPLE FROM A SURFACE TO BE ANALYZED

(71) Applicant: UT-BATTELLE, LLC, Oak Ridge, TN (US)

(72) Inventors: Gary J. Van Berkel, Oak Ridge, TN (US); Vilmos Kertesz, Knoxville, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 608 days.

(21) Appl. No.: 14/245,324

(22) Filed: Apr. 4, 2014

(65) Prior Publication Data

US 2014/0216177 A1    Aug. 7, 2014

Related U.S. Application Data (63) Continuation of application No. 12/380,980, filed on Mar. 5, 2009, now abandoned.

(51) Int. Cl.
| | |
|---|---|
| G01N 1/10 | (2006.01) |
| H01J 49/04 | (2006.01) |
| H01J 49/16 | (2006.01) |

(52) U.S. Cl.
CPC ...... *H01J 49/0431* (2013.01); *H01J 49/0463* (2013.01); *H01J 49/167* (2013.01); *G01N 2001/1031* (2013.01); *H01J 49/045* (2013.01)

(58) Field of Classification Search
CPC .... H01J 49/045; H01J 49/167; H01J 49/0463; H01J 49/0431; G01N 2001/1031
See application file for complete search history.

(56) References Cited

U.S. PATENT DOCUMENTS

| | | |
|---|---|---|
| 6,207,954 B1 | 3/2001 | Andrien, Jr. et al. |
| 6,620,625 B2 | 9/2003 | Wolk et al. |
| 6,803,566 B2 | 10/2004 | Van Berkel |
| 2002/0037367 A1* | 3/2002 | Ema .................... B05D 3/0254 427/240 |
| 2003/0080143 A1 | 5/2003 | Kale et al. |

(Continued)

FOREIGN PATENT DOCUMENTS

| | | |
|---|---|---|
| JP | 07159293 | 6/1995 |
| WO | 03090249 | 10/2003 |
| WO | 2006132708 | 12/2006 |

*Primary Examiner* — Daniel S Larkin
*Assistant Examiner* — Alex Devito
(74) *Attorney, Agent, or Firm* — Fox Rothschild LLP (57) ABSTRACT

A method and system for formation and withdrawal of a sample from a surface to be analyzed utilizes a collection instrument having a port through which a liquid solution is conducted onto the surface to be analyzed. The port is positioned adjacent the surface to be analyzed, and the liquid solution is conducted onto the surface through the port so that the liquid solution conducted onto the surface interacts with material comprising the surface. An amount of material is thereafter withdrawn from the surface. Pressure control can be utilized to manipulate the solution balance at the surface to thereby control the withdrawal of the amount of material from the surface. Furthermore, such pressure control can be coordinated with the movement of the surface relative to the port of the collection instrument within the X-Y plane.

18 Claims, 5 Drawing Sheets

(56) References Cited

U.S. PATENT DOCUMENTS

2003/0193020 A1* 10/2003 Van Berkel ........... H01J 49/165
250/288
2006/0082749 A1* 4/2006 Tokita ................. G03F 7/70341
355/53
2008/0156985 A1 7/2008 Venter et al.

* cited by examiner

METHOD AND SYSTEM FOR FORMATION AND WITHDRAWAL OF A SAMPLE FROM A SURFACE TO BE ANALYZED

CROSS REFERENCE TO RELATED APPLICATIONS

This application is a continuation of U.S. Nonprovisional application Ser. No. 12/380,980, filed Mar. 5, 2009, entitled "Method and System for Formation and Withdrawal of a Sample From a Surface to be Analyzed," the disclosure of which is incorporated fully by reference.

STATEMENT REGARDING FEDERALLY SPONSORED RESEARCH

This invention was made with government support under contract No. DE-AC05-00OR22725 awarded by the U.S. Department of Energy to UT-Battelle, LLC, and the government has certain rights in this invention.

BACKGROUND OF THE INVENTION

This invention relates generally to sampling means and methods and relates, more particularly, to the means and methods for formation and withdrawal of an amount of a sample from a surface desired to be analyzed.

The sample collection techniques with which this invention is to be compared involves the positioning of an instrument in relatively close proximity to a surface to be analyzed, or sampled, for purposes of gathering an amount of the surface, or more specifically, material from the surface, for analysis. An example of one such instrument used for sample-collecting purposes is in the form of a sampling probe including a pair of concentrically-arranged outer and inner tubes providing concentrically-arranged outer and inner flow passageways which open at a tip (i.e. a port-providing end) of the probe. During a sampling process performed with such a probe, the tip is placed in close proximity to the surface of a sample to be sampled, and a liquid eluting solution (e.g. a sample-dissolving solvent) is conducted onto the surface of the sample through the outer passageway. As the eluting solvent is conducted onto the sample surface, an amount of the sample from the surface is drawn into the inner passageway through the probe tip for sampling purposes.

An example of a collection instrument of the aforedescribed class is described in U.S. Pat. No. 6,803,566 having an inventor in common with the instant application.

It is an object of the present invention to provide a new and improved method and an associated system for formation of a sample (comprised of an amount of a sample-rich liquid solution) on a surface to be sampled and for withdrawing the formed sample from the surface.

Another object of the present invention is to provide such a method which accommodates the exposure of the sample to the liquid solution for a preselected period of time before an amount of sample is extracted for sampling purposes.

Still another object of the present invention is to provide such a method which is particularly well-suited for extracting samples from different sites across the surface of the sample for sampling purposes.

A further object of the present invention is to provide such a method which is well-suited for extracting samples from a surface which is not shaped so as to confine the liquid solution within a boundary.

A still further object of the present invention is to provide such a method which is uncomplicated to perform, yet effective in operation.

SUMMARY OF THE INVENTION

This invention resides in a method and a system for formation of a sample on and withdrawal of a formed sample from a surface to be analyzed.

The method includes the steps of providing an instrument having a port through which a liquid solution is conducted onto the surface to be analyzed and positioning the port of the instrument adjacent the surface to be analyzed. The liquid solution is then conducted onto the surface through the port of the instrument so that the liquid solution conducted onto the surface interacts with material comprising the surface. An amount of material is then withdrawn from the surface.

The surface sampling system includes an instrument having a port through which a liquid solution is conducted onto the surface to be analyzed and through which an amount of sample is withdrawn from the surface and means for positioning the port of the instrument adjacent the surface to be analyzed. In addition, the system includes means for conducting the liquid solution onto the surface through the port of the instrument so that the liquid solution conducted onto the surface interacts with material comprising the surface and means for withdrawing an amount of material from the surface through the port of the instrument.

DETAILED DESCRIPTION OF AN ILLUSTRATIVE EMBODIMENT

The invention will now be described in connection with an example of a embodiment, generally indicated 20 and schematically illustrated in FIG. 1, of an electrospray (ESI) system with which steps of the method of the invention can be carried out and within which features of the present invention are embodied for purposes of obtaining samples from at least one spot, or area, of a surface 22 (embodying a surface to be sampled) for subsequent analysis. Briefly stated, the method of the present invention can be performed with any of a number of suitable instruments, such as a pipet or syringe, which can be used to conduct a liquid solution onto the surface 22 so that the liquid solution interacts with material comprising the surface 22 and to thereafter withdraw an amount of material from the surface 22 as a sample. It will therefore be understood that the depicted system 22 shown and described herein is one example of a system with which the method of the invention can be performed.

Although the surface 22 to be sampled can, for example, be an array whose samples are desired to be analyzed with a mass spectrometer 23, the system 20 can be used to sample any of a number of surfaces of interest and is believed to be particularly useful in the readout of TLC plates, affinity arrays, and tissue sections. Accordingly, the principles of the invention can be variously applied.

Applicants have, in several instances, demonstrated the use of a combined liquid junction surface sampling probe (LMJ-SSP) as the interface for sampling surfaces for subsequent mass sprectrometric (MS) analysis. This device exploits a surface sampling probe-to-surface liquid microjunction and a self-aspirating electrospray ionization (ESI) or atmospheric pressure chemical ionization (APCI) emitter to sample material from surfaces. The analytical utility of these LMJ-SSP/ESI and LMJ-SSP/APCI couplings has been demonstrated by the qualitative and quantitative analysis of a variety of analytes separated on commercially available reversed-phase (RP) C8 and C18 thin layer chromatography (TLC) plates, affinity arrays and tissue sections. The width of the liquid junction was in the range of 20-60 µm in these prior instances. The formation of the sampling probe-to-surface liquid junction (20-60 µm in width) was later automated using image analysis. However, this automated method requires approximately 15-30 seconds to form the liquid junction, thereby preventing the LMJ-SSP to be considered as a practical interface in a high-throughput surface sampling system. As will be explained herein, the applicants have developed a methodology for collecting samples with the SSP equipment which is believed to be better suited for high throughput sampling purposes.

Figure 1:
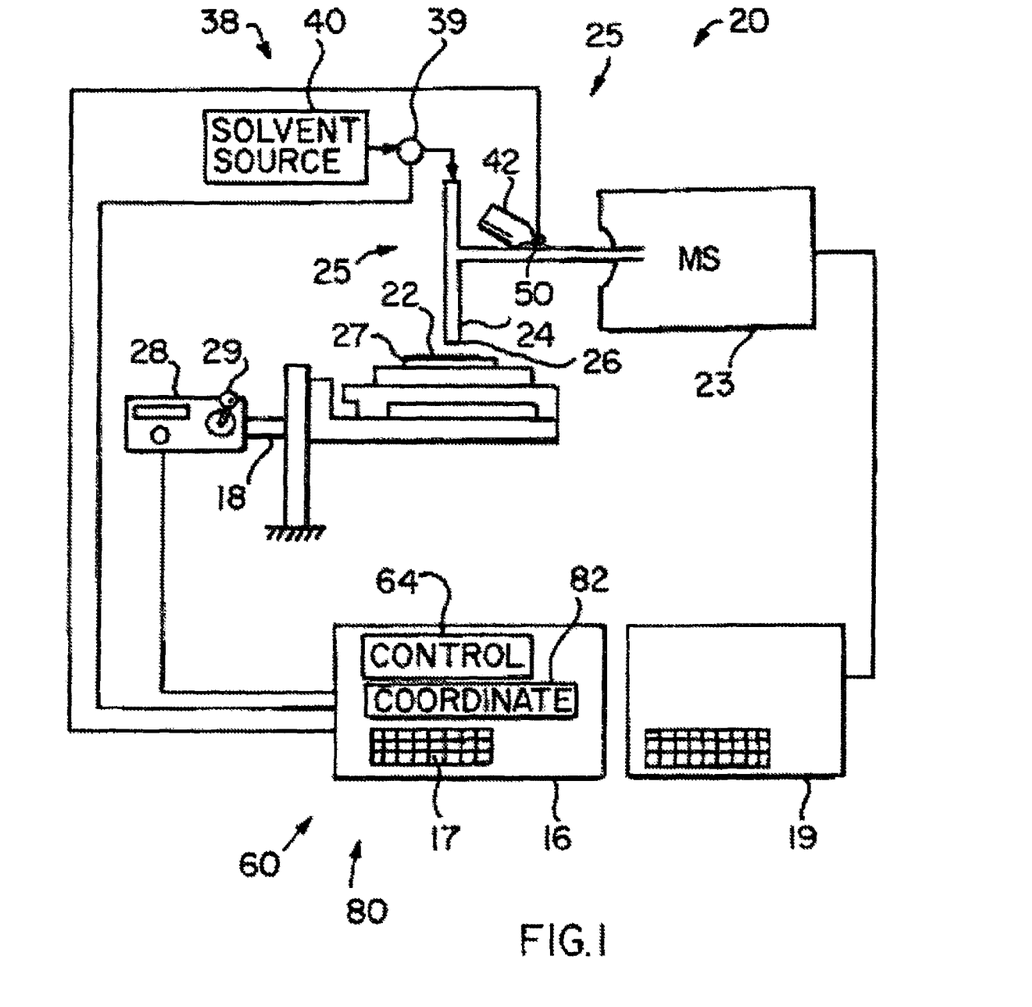
FIG. 1 is a schematic view of an example of a system within with features of the present invention are incorporated.
Figure 2:
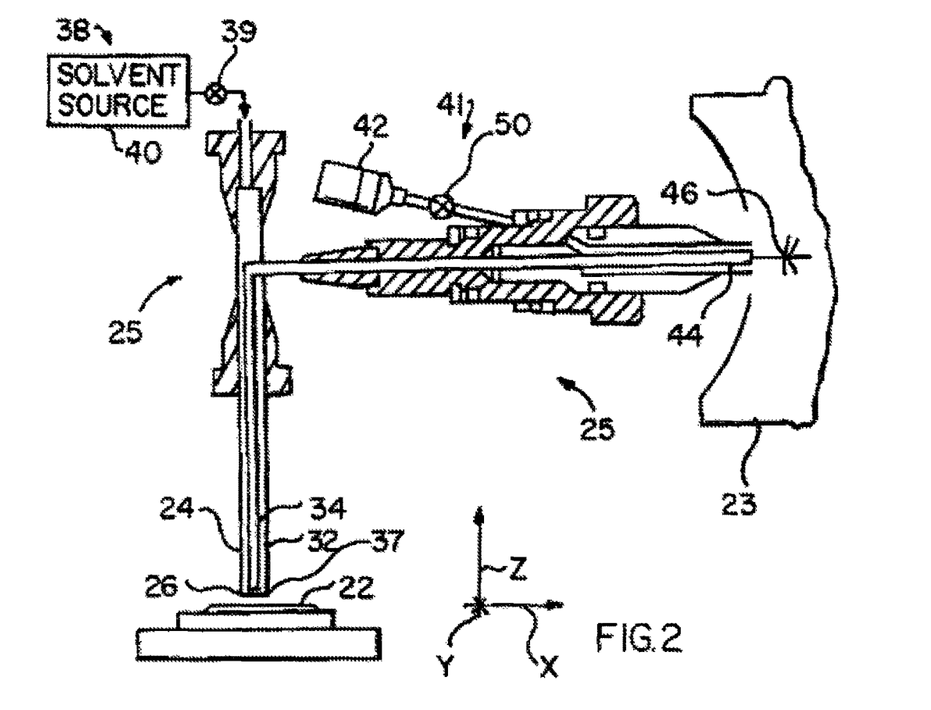
FIG. 2 is a longitudinal cross-sectional view of selected components, including the sample-collecting componentry, of the FIG. 1 system.
Figure 3:
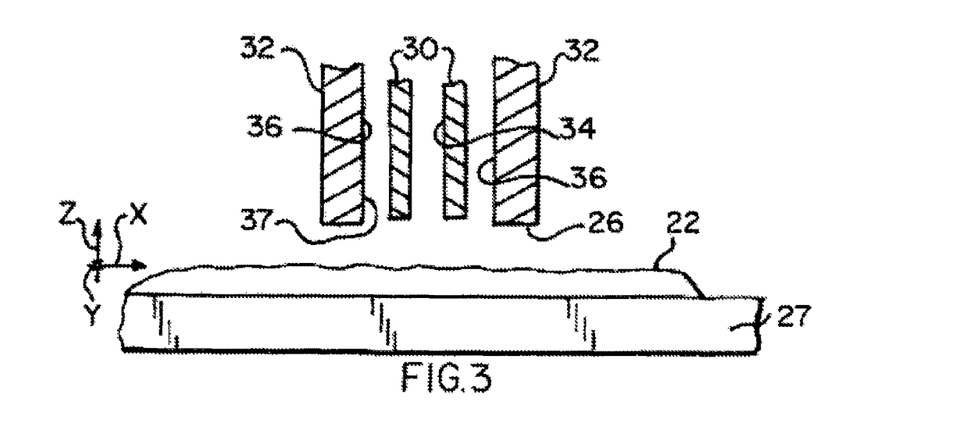
FIG. 3 is a longitudinal cross-sectional view of the tip end of the collection instrument used in the FIG. 1 system drawn to a larger scale.

With reference to FIGS. 1-3, the depicted system 20 includes sample-collecting componentry, generally indicated 25, including a collection instrument in the form of a surface sampling probe 24 which terminates at a tip 26 (providing a port 37) which, in turn, is positionable adjacent the surface 22 for the purpose of collecting samples from the surface 22. The sampling probe 24 of the depicted system 22 includes concentrically-arranged inner and outer tubes 30 and 32 (FIGS. 2 and 3) which provide inner and outer flow passageways 34 and 36, respectively, but it will be understood that a suitable instrument for carrying out the steps of the method of the present invention can take alternative forms.

The sample-collecting componentry 25 also includes means, generally indicated 38 in FIG. 2, for conducting a liquid sample-dissolving agent or solution, such as an eluting solvent, into the outer flow passageway 36 of the probe 24 for deposit upon the surface 22 to be sampled. To this end, the agent-conducting means 38 includes a source 40 of liquid agent and is connected in flow communication with the outer flow passageway 34 so that the liquid agent which is delivered into the outer passageway 34 is permitted to protrude from, and thus flow out of, the probe tip 26 for deposit upon the surface 22 in an atmospheric pressure environment. Control over the flow of the liquid solution into the outer passageway 34 can be had by way of pump (not shown) or an actuatable regulator, or valve 39, connected in-line with the flow of the liquid solution from the source 40 to the outer flow passageway 36.

The sample-collecting componentry 25 also includes means, generally indicated 41 in FIG. 2, for delivering a flow of nebulizing gas in such a relationship to the probe 24 to alter the pressure therein. Such delivery means 41 includes a source 42 of nebulizing gas, under pressure, which is routed past the distal end, indicated 44, of the probe 24 (i.e. the probe end opposite the tip 26). By directing the flow of nebulizing gas past the end 44 of the probe 24 at a high enough flow rate, an amount of sample situated adjacent the probe tip 26 is withdrawn from the surface 22 (due to the pressure differential created between the end 44 and the tip 26 of the probe 24) and transported toward the mass spectrometer 23 by the nebulizing gas in a spray 46 for analysis of the collected sample. The flow of the nebulizing gas from the source 42 can be controlled by way of an actuatable regulator or valve 50 connected in-line with the flow of nebulizing gas directed from the source 42.

During operation of the system 20, the probe tip 26 is positioned adjacent a site on the surface 22 and an amount of liquid solution, or agent, is permitted to flow from the source 40 and through the outer passageway 34 of the probe 24 so that the liquid solution is conducted out of the probe tip 26 and deposited onto the surface 22 where the liquid solution is permitted to interact with the material comprising the surface 22. When it is desired to collect an amount of material of the surface 22, the flow rate of the nebulizing gas is directed past the distal end 44 of the probe 24 so that an amount of sample, along with the deposited solution, is drawn upwardly from the surface 22 through the inner passageway 32 and transported out of the distal end 44 of the probe 24 in a spray 46 (FIG. 2).

Figure 4:
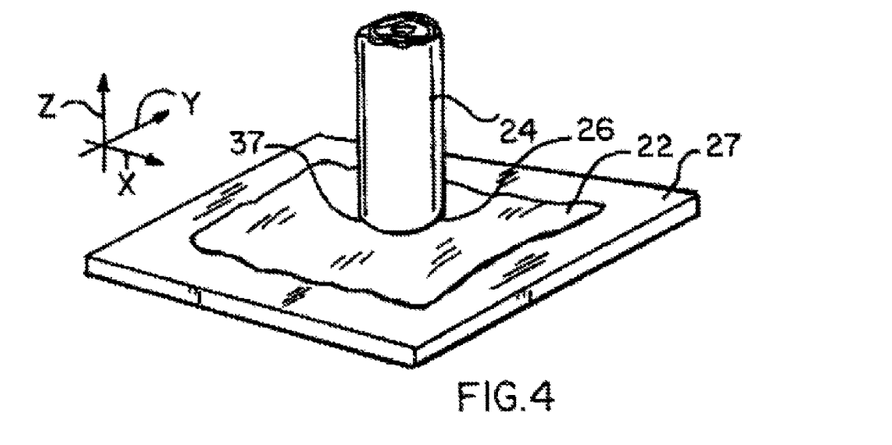
FIG. 4 is a perspective view of the tip end of the collection instrument depicted in FIG. 3 and a view of the surface from which a sample is desired to be collected.

With reference to FIGS. 3 and 4, there is illustrated an example of a surface 22 from which an amount of sample is desired to be collected for analysis. Within the depicted surface 22, the sample is spread across and thereby disposed generally within the indicated X-Y coordinate plane. To enable samples to be collected from any X-Y coordinate site, spot or location, across the surface 22 to sampled, the probe 24, along with its tip 26, is supported in a fixed, stationary condition, with respect to the surface 22 to be sampled, and the surface 22 is, in turn, supported upon a support plate 27 for movement relative to the probe tip 26 along the indicated X-Y coordinate axes, i.e. within the plane of the support plate 27, and toward and away from the probe tip 26 along the indicated Z-coordinate axis. The support plate 27 of the depicted system can take the form, for example, of a thin-layer chromatography (TLC) plate upon which an amount of material desired to be analyzed is positioned. It follows that for purposes of discussion herein, the surface 22 to be sampled is supported by the support plate 27 within an X-Y plane, and the Z-axis is perpendicular to the X-Y plane.

With reference again to FIG. 1, the support plate 27 is, in turn, supportedly mounted upon the movable support arm 18 of an XYZ stage 28 (FIG. 1) for movement of the support plate 27, and the surface 22 supported thereby, along the indicated X, Y and Z coordinate directions. The XYZ stage 28 is appropriately wired to a joystick control unit 29 which is, in turn, connected to a first control computer 16 for receiving command signals therefrom so that during a sampling process performed with the system 20, samples can be taken from any desired site (i.e. any desired X-Y coordinate location) along the surface 22 or along any desired lane (i.e. along an X or Y-coordinate path) across the surface 22 as the surface 22 is moved within the X-Y plane beneath the collection tube tip 26.

For example, there is illustrated in FIGS. 3 and 4 a view of the probe 24 arranged in a sample-collecting position above the surface 22 for collecting samples from the surface 22. To re-position the probe tip 26 in a sample-collecting position adjacent, or above, an alternative X-Y coordinate site across the surface 22, the surface 22 is appropriately indexed beneath the probe tip 26 to re-position the probe tip 26 adjacent the desired surface site from which an amount of sample is desired to be collected. The characteristics of the relative movements of the surface 22 and the probe tip 26, such as the sweep speeds and the identity of the X-Y locations at which the probe 24 is desired to be positioned in sample-collecting registry with the surface 22 can be input into the computer 16, for example, by way of a computer keyboard 17 or pre-programmed within memory of the computer 16.

Although a description of the internal components of the XYZ stage 28 is not believed to be necessary, suffice it to say that the X and Y-coordinate position of the support surface 27 (and surface 22) relative to the probe tip 26 is controlled through the appropriate actuation of, for example, a pair of reversible servomotors (not shown) mounted internally of the XYZ stage 28, while the Z-coordinate position of the support surface 27 (and surface 22) relative to the probe tip 26 is controlled through the appropriate actuation of, for example, a reversible stepping motor (not shown) mounted internally of the XYZ stage 28. Therefore, by appropriately energizing the X and Y-coordinate servomotors, the surface 22 can be positioned so that the tip 26 of the probe 24 can be positioned in sample-collecting registry with any X-Y coordinate site within the X-Y coordinate plane of the surface 22, and by appropriately energizing the Z-axis stepping motor, the surface 22 can be moved toward or away from the probe tip 26.

With reference again to FIG. 1, the depicted system 20 further includes a mass spectrometer 23 which is situated adjacent the sample-collecting componentry 25 (FIG. 2) for accepting the sample-including spray 46 conducted thereto for purposes of analysis, and there is associated with the mass spectrometer 23 a second control computer 19 for controlling the operation and functions of the mass spectrometer 23. An example of a mass spectrometer suitable for use with the depicted system 20 as the mass spectrometer 23 is available from MDS SCIEX of Concord, Ontario, Canada, under the trade designation 4000 Qtrap. Although two separate computers 16 and 19 are utilized within the depicted system 20 for controlling the various operations of the system components (including the mass spectrometer 23), all of the operations performed within the system 20 can, in the interests of the present invention, be controlled with a single computer or, in the alternative, be controlled through an appropriate software component loaded within the mass spectrometer software package. In this latter example, a single software package could control the XYZ staging and the mass spectrometric detection.

During a sample-collecting operation performed with the system 20, the surface 22 and probe 24 are moved relative to one another, as necessary, along X and Y-coordinate directions to position the probe tip 26 in sample-collecting (i.e. stationary position) registry with the surface 22 at a desired X-Y coordinate location with the surface 22 for the purpose of collecting a sample from the desired X-Y coordinate location at the surface 22. To this end, appropriate commands signals are sent from the computer 16 to the motors associated with the XYZ stage 28 to position the probe tip 26 in sample-collecting registry with a desired X-Y coordinate location on the surface 22. The actuatable valve 39 is then opened to permit a flow of liquid solution onto the surface 22 through the probe tip 26 by way of the outer flow passageway 36 to thereby expose the surface 22 to the liquid agent. The actuatable valve 50 is also opened to permit the nebulizing gas to flow in sequence through the valve 50 and past the distal end 44 of the probe 26 to thereby lower the pressure thereat. Due to the created pressure differential between the distal end 44 and the tip 26 of the probe 24, an amount of the sample (e.g. material indicated 52 in FIG. 5) from the surface 22, along with the amount of liquid solution which has been conducted from the source 40, for transport to the mass spectrometer 23 for analysis.

Figure 5:
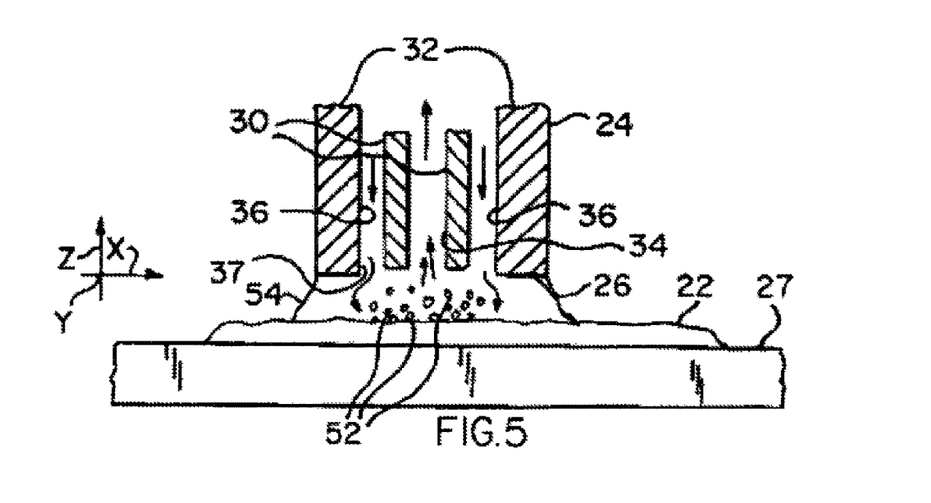
FIG. 5 is a view similar to that of FIG. 3 but illustrating the formation of a junction at the interface of the collection instrument and the surface from which a sample is desired to be collected.

It is a feature of the depicted system 20 that it includes means, generally indicated 60 in FIG. 1, for controlling the flow of nebulizing gas directed through the valve 50 to thereby control the formation of a sample with the liquid solution conducted to the surface 22 and the subsequent withdrawal of the sample (i.e. in the form of a sample-rich junction, indicated 54 in FIG. 5, from the surface 22 with the probe 24. Within the depicted system 20, the control means 60 includes the valve 50, introduced earlier, which is connected in-line with the flow of nebulizing gas conducted past the distal end 44 of the probe 24 and control circuitry 64 mounted, for example, within the computer 16 and connected to the valve 50 for altering the flow rate of the nebulizing gas moving through the valve 50 as desired. In other words and during a sample-collecting operation performed with the system 20, the control circuitry 64 sends appropriate command signals to the valve 50 for selectively adjusting the valve 50 to thereby adjust the flow rate of nebulizing gas between a reduced condition and a normal sample-withdrawing, or elevated, condition.

More specifically, by appropriately adjusting the valve 50, the flow rate of nebulizing gas through the valve 50 is either lowered to a level, or condition, of reduced flow which is insufficient to effect the withdrawal of a sample from the surface 22 or raised to a level, or condition, of elevated flow which is sufficient to effect the withdrawal of a sample from the surface 22. As long as the valve 50 is maintained in its reduced flow condition, no sample will be withdrawn from the surface 22 through the probe 24, and as long as the valve 50 is maintained in its elevated flow condition (which is normal for sample-collecting purposes), an amount of sample will be withdrawn from the surface 22 for analysis. It will be understood that the control circuitry 64, mentioned earlier, which controls the adjustment of the valve 50 generates commands for adjustments of the valve 50 in accordance with commands which have been previously input into the computer 16 by an operator. In any event, the operation of the depicted system 20 is fully computer-controlled and does not require operator intervention.

In one aspect of a sample-collecting process during which the control means 60 are utilized to adjust the flow rate of nebulizing gas through the valve 50, the probe tip 26 is disposed in a stationary and sample-collecting relationship with a desired X-Y coordinate location over the surface 22 and the valve 50 is maintained in a reduced flow condition to thereby prevent the collection of a sample from the surface 22. Under these circumstances, the sample-collecting componentry 25 is maintained in a standby mode during which no sample is collected from the surface 22, although liquid solution continues to be conducted onto the surface 22 through the probe tip 26. Thereafter and when it is desired to collect an amount of sample from the surface 22, the valve 50 is returned to its condition of increased flow to thereby switch the sample-collecting componentry 25 to a collection mode and initiate the collection of an amount of sample from the surface 22. It follows that by repeatedly adjusting the valve 50 between the reduced and increased flow conditions, a number of samples are collected in sequence from the surface 22.

The capacity to control the flow rate of nebulizing gas through the valve 50 permits an operator to accurately control the instances and/or intervals at which samples are collected from the surface 22. Furthermore and since the flow of liquid solution continues to be conducted upon the surface 22 even after the flow rate of nebulizing gas is reduced, the liquid solution continues to collect, or build-up, upon the surface 22. Such a permitted build up can be advantageous in two respects. Firstly, rather than positioning the probe tip 26 at a relatively precise probe-to-surface spaced distance in preparation of a sample-collecting operation, the probe tip 26 can be positioned at a spaced distance which is slightly greater than the relatively precise probe-to-surface distance because as the liquid solution is permitted to accumulate upon the surface 22, the height of the accumulated build up increases to a height necessary to create the desired junction 54 which extends between the surface 22 and the probe tip 26. In other words, the permitted build up of liquid solution upon the surface 22 reduces the accuracy, or criticality, with which the probe tip 26 must be initially spaced from the surface 22 in preparation of a sample-collecting operation.

Secondly, the permitted build up is advantageous in a situation in which it is desirous that the surface 22 be exposed to the liquid solution for a selected period of time before the sample is collected from the surface 22. In other words, the longer that a build-up of liquid solution rests upon the surface 22, the longer the period of time that the liquid solution can interact with (or act upon) the surface 22 before a sample is withdrawn from the surface 22 for analysis. Thus, the operation of the system 22 can be pre-programmed to delay the collection of a sample for a preselected period of time (e.g. for a few seconds or more) following the conductance of the liquid solution onto the surface 22.

It is another feature of the system 20 that it includes means, generally indicated 80 in FIG. 1, for coordinating the flow rate of nebulizing gas past the distal end 44 of the probe 24 with the movement of the surface 22 relative to the probe tip 26 within the X-Y coordinate plane. To this end and within the depicted system 20, the coordinating means 80 includes control circuitry 82 mounted within, for example, the computer 16 so that the flow of nebulizing gas is permitted to flow through the valve 50 at conditions (i.e. preselected conditions) determined by the relative movements and/or positions between the surface 22 and the probe tip 26.

In one aspect of a sampling operation performed with the system 20, the control means 80 permits the nebulizing gas to flow through the valve 50 at the increased, or elevated, flow rate only when the probe tip 26 is disposed in a stationary relationship with the surface 22 for the purpose of collecting a sample therefrom and maintains the flow of nebulizing gas through the valve 50 at the reduced flow rate as long as the surface 22 and probe tip 26 are being moved relative to one another. In other words, the control means 80 prevents the flow of nebulizing gas through the valve 50 at the increased flow rate as long as the surface 22 is being moved relative to the probe tip 26 within the X-Y coordinate plane so that no sample is collected from the surface 22 while the relative movement between the surface 22 and the probe tip 26 is underway. Inasmuch as the flow of liquid solution onto the surface 22 is believed to slightly increase as long as a sample-withdrawing vacuum is being created at the probe tip 26, such a coordination between the X-Y movement of the surface 22 relative to the probe tip 26 and the control of the flow rate of nebulizing gas through the valve 50 is believed to conserve the liquid solution by reducing the conducted flow of liquid solution onto the surface 22 until such moment as an amount of sample is desired to be collected from the surface 22.

In another aspect of a sampling operation performed with the system 20, the coordinating means 80 maintains the flow of nebulizing gas through the valve 50 at the increased flow rate as long as the surface 22 and probe tip 26 are being moved relative to one another and permits the flow of nebulizing gas through the valve 50 at the reduced flow rate only after the probe tip 26 has been disposed in a stationary, sample-collecting relationship with the surface 22 for a preselected period of time. Under these circumstances, the liquid solution which is conducted to the surface 22 is permitted to build up upon the surface 22 before a sample is collected therefrom. As mentioned earlier, the preselected period of time provides time during which the liquid solution can interact with the material which comprises the surface 22 and can be advantageous in this respect.

It follows from the foregoing that a method and associated system 20 have been described for sampling a surface 22 to be analyzed. A collection instrument 24 is provided and then its tip 26 is positioned adjacent the surface 22 and in sample-collecting registry therewith. The liquid solution from the source 40 is thereafter conducted onto the surface 22 through the tip 26. By controlling the flow of nebulizing gas which, in turn, effects the creation of a sample-withdrawing vacuum at the tip of the collection instrument 26, the collection of an amount of sample from the surface 22 with the collection instrument 24 is controlled.

The associated system 20 includes means for positioning the tip 26 of the probe 24 adjacent the surface 22 to be analyzed and means for conducting liquid solution from a source 40 onto the surface 22 through the tip 26. By controlling the rate of flow of nebulizing gas from a source 42 past the distal end 44 of the probe 24, characteristics such as instances and intervals at which samples can be collected can be controlled. In this connection, control means 60 are included within the system 20 for controlling the flow rate of nebulizing gas to thereby control the characteristics (e.g. instances and intervals between successive sample-withdrawal steps) of a sample-collection process.

In the situation in which the surface 22 includes a plurality of X-Y coordinate sites from which samples are desired to be collected, the system also includes coordinating means 80 for coordinating the movement of the surface 22 relative to the probe 24 in the X-Y coordinate plane and the flow rate of nebulizing gas to control various characteristics of the sample-collecting process wherein such characteristics can include, but are not limited to, the instances, the X-Y coordinate locations from which samples are desired to be collected, the duration of each sample-withdrawal step and the time intervals between successive sample-withdrawing steps. If desired, the movement between the probe 24 and the surface 22 within the X-Y coordinate plane and the flow rate of nebulizing gas can be coordinated so that no sample is withdrawn from the surface 22 as long as the surface 22 and the probe 24 are being moved relative to one another.

Figure 6A:
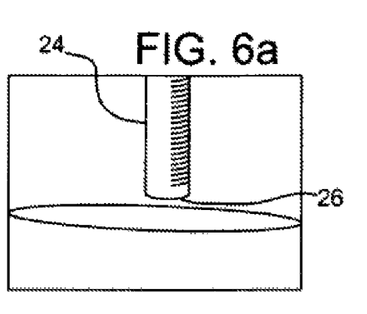
FIGS. 6a-6h are captured images taken from one side of the collection instrument of FIGS. 3-4 illustrating in sequence the development of a liquid junction and the subsequent withdrawal of the developed junction from the surface through the collection instrument.
Figure 6B:
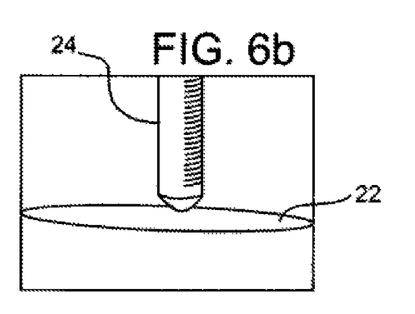
Figure 6C:
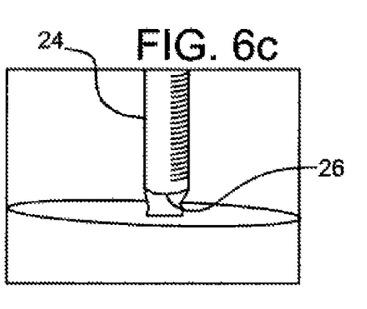
Figure 6D:
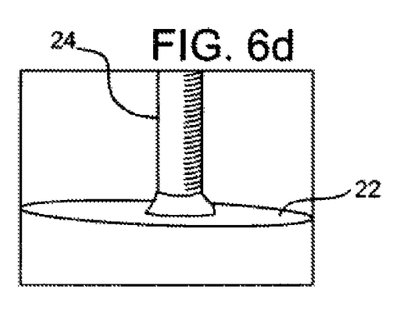
Figure 6E:
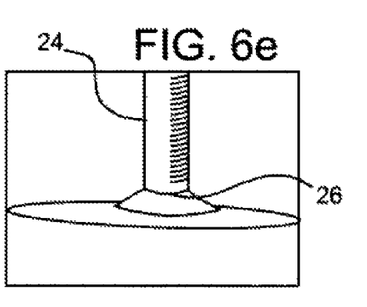
Figure 6F:
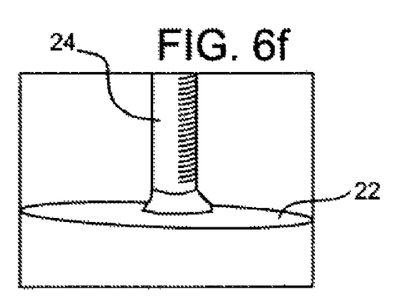
Figure 6G:
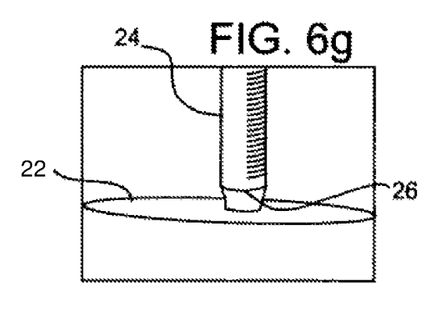
Figure 6H:
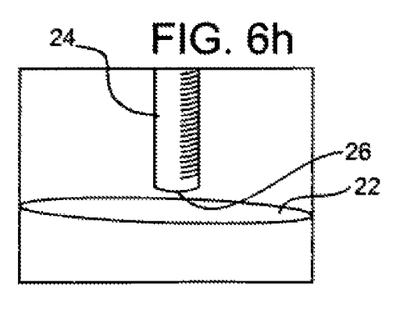

With reference to FIGS. 6a-6h, there are shown captured images taken from one side of the collection instrument illustrating in sequence the development of a junction and subsequent withdrawal of a sample from the surface as the flow rate of the nebulizing gas is adjusted between reduced flow conditions and increased, or normal, flow condition for collecting a sample from the surface. For example, in FIG. 6a, the collection probe 24 is positioned above the surface spot to be analyzed, and the nebulizer gas flow rate is normal. In FIGS. 6b through 6e, the nebulizer gas flow rate is reduced to and maintained in its reduced flow rate condition so that the liquid solution conducted upon the surface begins to build up upon the surface. In FIGS. 6f through 6h, the normal nebulizer gas flow rate is resumed (i.e. elevated to its increased condition, or pre-analysis level) so that an analyte-rich solution composing the junction is collected and aspirated.

It can be seen from the views of FIGS. 6b through 6e, the area or spot over which the sample is covered by the liquid solution increases in size (i.e. diameter) as the liquid solution accumulates upon the surface. Such an occurrence can be advantageous in that the solution which is subsequently withdrawn from the surface for analysis contains sample amounts from the relatively broad area covered by the liquid agent.

The aforedescribed system and method has been tested and automates the formation and withdrawal of a liquid microjunction (LMJ) having an approximate width of (but which is not limited to) about 150-300 μm for analytical advantage using a probe having a width of approximately 650 μm First, the LMJ-SSP is positioned at a specific distance (between about 150-300 μm) above a surface plot to analyze, followed by reducing the nebulizer gas flow rate that allows the liquid solution to protrude from the tip 26 (i.e. the sampling end) of the probe 24. While the nebulizer gas flow rate is in the reduced flow condition, the liquid solution protruding from the probe tip 26 is permitted to accumulate upon the surface 22 to form a liquid junction and to dissolve analytes from the surface 22. After a preselected, or desired, period of time has passed, the nebulizer gas flow rate is raised, or returned, to its pre-analysis level, thereby allowing the analyte-rich solution composing the junction to be collected and aspirated. With this capability, applicants have demonstrated automated spot sampling from a surface of matrix-assisted laser desorption (MALDI) plates and a guinea pig brain tissue section. Thus, novelty lies in the methodology, i.e. allowing the protruding solution to form a junction and dissolve the analyte, and withdrawing the analyte-rich solution of the junction by manipulating the solution balance in the sampling probe by way of pressure control. Other means for manipulating the solution balance in the sampling probe can include, but is not limited to: changing the applied electrospray voltage; applying a voltage program to the surface; and changing the solution flow rate.

Figure 7A:
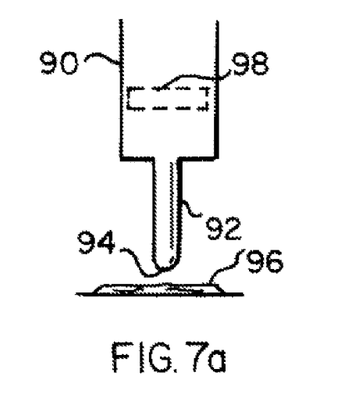
FIGS. 7a-7c are side elevational views depicting schematically the steps of the method of the invention being carried out with a pipet.
Figure 7B:
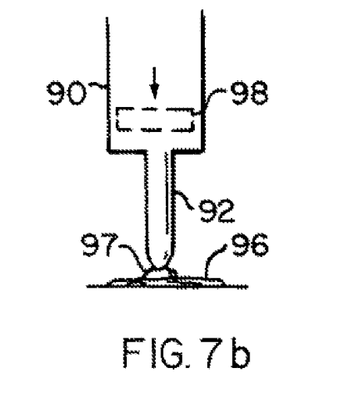
Figure 7C:
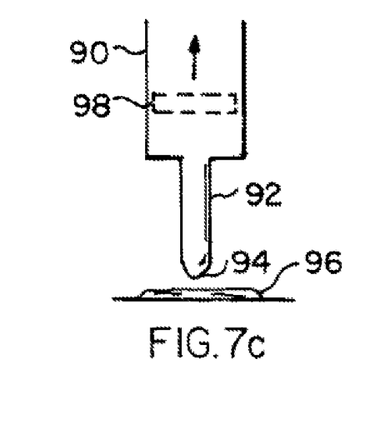

Moreover, the sampling method described herein can be used with an alternative probe system (for example, a similar SSP or a pipet or syringe) through which a solution is both dispensed and retrieved (i.e. collected) from the surface for analysis by another method rather than the on-line, continuous flow type of analysis described herein. For example, there is illustrated in FIGS. 7a-7c views depicting the carrying out of steps of the method of the invention with a pipet 90 having a dispensing and collection tube 92 provided with a port 94 at the end thereof. More specifically and as illustrated in FIG. 7a, the pipet 90 is positioned adjacent a surface 96 to be analyzed so that the port 94 is disposed in relatively close proximity to the surface 96. Thereafter and as illustrated in FIG. 7b, an amount of liquid solution, indicated 97 in FIG. 7b, is conducted onto the surface 96 through the port 94 (to permit the liquid solution 97 to interact with the surface 96) as a plunger, indicated 98, associated with the pipet 90 is moved through the body of the pipet 90 and toward the tube 92. Thereafter, the plunger 98 is retracted through the body of the pipet 90 to withdraw an amount of the sample-rich solution into the tube 92 through the port 94 thereof. The withdrawn sample-rich solution could be immediately sampled or transferred to an injection loop, another work station, or another instrument for measurement or processing such as any type of solid phase extraction, chromatographic or other liquid phase separation or mass spectrometric measurement.

It will be understood that numerous modifications and substitutions can be had to the aforedescribed embodiment without departing from the spirit of the invention. For example and although the system 20 has been shown and described as including a probe 24 whose collection tip 26 is arranged substantially along a vertical axis and above the surface 22 for collection of an amount of sample from the surface 22, the collection tip 26 and surface 22 (although commonly arranged at right angles with respect to one another) can be arranged in any of a number of orientations. For example, the surface 22 can be disposed horizontally (i.e. within a Y-Z coordinate plane) with the probe tip 26 arranged adjacent the surface 22 so that its axis is parallel to the X-coordinate axis. In this or any other such arrangement, the surface tension between the liquid solution conducted to the surface 22 is large enough that the liquid solution does not drip or flow from the surface 22 due to gravity. Consequently, the system 22 and process described herein is particularly well-suited for use in collecting samples from a surface which does not require that a liquid solution be confined, as within a well, over an area of a surface to be sampled.

Accordingly, the aforedescribed embodiments are intended for the purpose of illustration and not as limitation.

We claim:
1. A system for sampling a surface, comprising:
a surface sampling probe defining a solvent liquid supply conduit and a sample liquid removal conduit, the solvent liquid supply conduit being connectable to a solvent source, the surface sampling probe having a tip, the solvent liquid supply conduit having an outlet opening at the tip, and the sample liquid removal conduit having an inlet opening at the tip;
a first flow control for controlling the flow rate of solvent liquid from the solvent source to the outlet opening of the solvent liquid supply conduit at the tip;
a gas inlet in fluid communication with a distal region of the sample liquid removal conduit for directing a flow of gas in a manner and at a flow rate sufficient to withdraw the sample liquid from sample liquid removal conduit;
a second flow control for controlling the flow rate of gas through the gas inlet and thereby the flow rate of sample liquid through the sample liquid removal conduit; the first flow control for controlling the flow rate of solvent liquid and the second flow control for controlling the flow rate of gas being independently adjustable to provide for the selection between at least a solvent liquid deposit condition where the flow rate of solvent liquid through the solvent liquid supply conduit exceeds the flow rate of sample liquid through the sample liquid removal conduit, and a sample liquid removal condition where the flow rate of solvent liquid through the solvent liquid supply conduit is less than the flow rate of sample liquid through the sample liquid removal conduit.

2. The system of claim 1, wherein the surface sampling probe comprises an outer tube and an inner tube, the outer and inner tubes defining the solvent liquid supply conduit and the sample liquid removal conduit.

3. The system of claim 2, wherein the outer tube defines the solvent liquid supply conduit and the inner tube defines the sample liquid removal conduit.

4. The system of claim 1, wherein the surface to be sampled is disposed substantially within an X-Y plane and is spaced from the probe along a Z-coordinate axis, and wherein the system further includes means for moving the surface and the probe relative to one another within the X-Y plane so that any number of X-Y coordinate locations along the surface can be positioned adjacent the probe for sample-collecting purposes.

5. The system of claim 4, further comprising a processor, the processor directing the means for moving the probe relative to the sample surface to X-Y coordinates for sample collecting purposes.

6. The system of claim 5, wherein the processor is operable to control at least one of the first flow control for controlling the flow rate of solvent liquid from the solvent source to the outlet opening of the solvent liquid supply conduit at the tip, and the second flow control for controlling the flow rate of gas through the gas inlet and thereby the flow rate of sample liquid through the sample liquid removal conduit.

7. The system of claim 6, wherein the processor controls at least one of the first flow control for controlling the flow rate of solvent liquid from the solvent source to the outlet opening of the solvent liquid supply conduit at the tip, and the second flow control for controlling the flow rate of gas through the gas inlet and thereby the flow rate of sample liquid through the sample liquid removal, so as to select between at least a solvent liquid deposit condition where the flow rate of solvent liquid through the solvent liquid supply conduit exceeds the flow rate of sample liquid through the sample liquid removal conduit, and a sample liquid removal condition where the flow rate of solvent liquid through the solvent liquid supply conduit is less than the flow rate of sample liquid through the sample liquid removal conduit.

8. The system of claim 1, further comprising a processor, the processor being operable to control at least one of the first flow control for controlling the flow rate of solvent liquid from the solvent source to the outlet opening of the solvent liquid supply conduit at the tip, and the second flow control for controlling the flow rate of gas through the gas inlet and thereby control the flow rate of sample liquid through the sample liquid removal conduit.

9. The system of claim 1, wherein the gas inlet is a nebulizing gas inlet.

10. A method of sampling a surface, comprising the steps of:
providing a surface sampling probe system, the system comprising a surface sampling probe defining a solvent liquid supply conduit and a sample liquid removal conduit, the solvent liquid supply conduit being in liquid communication with a solvent source, the surface sampling probe having a tip, the solvent liquid supply conduit having an outlet opening at the tip, and the sample liquid removal conduit having an inlet opening at the tip; the surface sampling probe system further comprising a first flow control for controlling the flow rate of solvent liquid from the solvent source to the outlet opening of the solvent liquid supply conduit at the tip; a gas inlet in fluid communication with a distal region of the sample liquid removal conduit for directing a flow of gas in a manner and at a flow rate sufficient to withdraw sample liquid from the sample liquid removal conduit; and a second flow control for controlling the flow rate of gas through the gas inlet and the flow rate of sample liquid through the sample liquid removal conduit; and,
independently controlling the first flow control for controlling the flow rate of solvent liquid and the second flow control for controlling the flow rate of gas so as to provide for the selection between at least a solvent liquid deposit condition where the flow rate of solvent liquid through the solvent liquid supply conduit exceeds the flow rate of sample liquid through the sample liquid removal conduit, and a sample liquid removal condition where the flow rate of solvent liquid through the solvent liquid supply conduit is less than the flow rate of sample liquid through the sample liquid removal conduit.

11. The method of claim 10, wherein the surface sampling probe comprises an outer tube and an inner tube, the outer and inner tubes defining the solvent liquid supply conduit and the sample liquid removal conduit.

12. The method of claim 11, wherein the outer tube defines the solvent liquid supply conduit and the inner tube defines the sample liquid removal conduit.

13. The method of claim 10, wherein the surface to be sampled is disposed substantially within an X-Y plane and is spaced from the probe along a Z-coordinate axis, and wherein the method further includes the step of moving the surface and the probe relative to one another within the X-Y plane so that a plurality of X-Y coordinate locations along the surface are positioned adjacent the probe for sample-collecting purposes.

14. The method of claim 13, further comprising a processor, the processor directing the moving of the probe relative to the sample surface to X-Y coordinates for sample collecting purposes.

15. The method of claim 14, wherein the processor operates to control at least one of the first flow control for controlling the flow rate of solvent liquid from the solvent source to the outlet opening of the solvent liquid supply conduit at the tip, and the second flow control for controlling the flow rate of gas through the gas inlet and thereby the flow rate of sample liquid through the sample liquid removal conduit.

16. The method of claim 15, wherein the processor controls at least one of the first flow control for controlling the flow rate of solvent liquid from the solvent source to the outlet opening of the solvent liquid supply conduit at the tip, and the second flow control for controlling the flow rate of gas through the gas inlet and thereby control the flow rate of sample liquid through the sample liquid removal, so as to select between at least a solvent liquid deposit condition where the flow rate of solvent liquid through the solvent liquid supply conduit exceeds the flow rate of sample liquid through the sample liquid removal conduit, and a sample liquid removal condition where the flow rate of solvent liquid through the solvent liquid supply conduit is less than the flow rate of sample liquid through the sample liquid removal conduit.

17. The method of claim 10, further comprising a processor, the processor operating to control at least one of the first flow control for controlling the flow rate of solvent liquid from the solvent source to the outlet opening of the solvent liquid supply conduit at the tip, and the second flow control for controlling the flow rate of nebulizing gas through the gas inlet and thereby the flow rate of sample liquid through the sample liquid removal conduit.

18. The method of claim 10, wherein the gas flow nebulizes the sample liquid.

* * * * *